(12) United States Patent
Breitenbucher et al.

(10) Patent No.: US 6,872,834 B2
(45) Date of Patent: Mar. 29, 2005

(54) PHENYL-SUBSTITUTED INDOLES AND INDAZOLES

(75) Inventors: J. Guy Breitenbucher, Escondido, CA (US); Wenying Chai, San Diego, CA (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/820,438

(22) Filed: Mar. 29, 2001

(65) Prior Publication Data

US 2002/0006928 A1 Jan. 17, 2002

Related U.S. Application Data

(60) Provisional application No. 60/194,071, filed on Mar. 31, 2000.

(51) Int. Cl.$^7$ ............................................. C07D 209/52
(52) U.S. Cl. ...................................................... 548/452
(58) Field of Search ................................ 548/452, 511, 548/467; 514/415, 414, 339, 323, 254.09; 546/277.4, 201; 544/373

(56) References Cited

U.S. PATENT DOCUMENTS

| 338,106 A | 3/1886 | Roper |
|---|---|---|
| 5,385,912 A | 1/1995 | Neuenschwander et al. |
| 5,681,954 A | 10/1997 | Yamamoto et al. |

FOREIGN PATENT DOCUMENTS

| WO | WO 97/44319 A1 | 11/1997 |
|---|---|---|
| WO | WO 98/06703 A1 | 2/1998 |
| WO | WO 98/067703 | * 2/1998 |
| WO | WO 98/48797 A1 | 11/1998 |
| WO | WO 98/48797 | * 11/1998 |
| WO | WO 99/33822 A1 | 7/1999 |
| WO | WO 00/04017 A1 | 1/2000 |

OTHER PUBLICATIONS

CAS printout of Plantier et al. (FR M3460).*
CAS printout of Buu–Hoi et al. Chem. Abs. 68:114411, 1968.*
CAS printout of Suh et al. Chem. Abs. 69:77112, 1968.*
CAS printout for Johsi et al.*
CAS printout for Agarwal et al.*
Robert Gastpar, Michael Goldbrunner, Doris Marko and Erwin Von Angerer, "Methoxy–Substituted 3–Formyl–2–phenylindoles Inhibit Tubulin Polymerization", J. Med. Chem., 1998, pp. 4965–4972, vol. 41.
Brad R. Henke, Kimberley K. Adkinson, Steven G. Blanchard, Lisa M. Lessnitzer, Robert A. Mook, Jr. Kelli D. Plunket, John A. Ray, Claudia Roberson, Rayomand Unwalla and Timothy M. Wilson, "Synthesis and Biological Activity of a Novel Series of Indole–Derived PPAR γ Agonists", Biooragnic & Medicinal Chemistry Letters 9, 1999, pp. 3329–3334.
George W. Kabalka, Lei Wang, Vasudevan Namboodiri and Richard M. Pagni, "Rapid Microwave–Enhanced, Solventless Sonogashira Coupling Reaction on Alumina", Tetrahedron Letters 41, 2000, pp. 5151–5154.
Surat Kumar and Shri Nivas Rastogi, "1–[Benzofuranyloxy– & p–(Cyclopent–2–en–1–yl/indolyl)phenoxy]–3–Substituted–amino–propan–2–ols propanes as Potential Biodynamic Agents", Indian Journal of Chemistry, Jul. 1983, pp. 659–663, vol. 22B.
Kazuhiro Miwa, Toyohiko Aoyama and Takayuki Shioiri, "Extension of the Colvin Rearrangement Using Trimethylsilyldiazomethane. A New Synthesis of Alkynes", Synlett, Feb. 1994, pp. 107–108.
Yutaka Nishiyama, Ryo Maema, Kengou Ohno, Masaharu Hirose, and Noboru Sonoda, "Synthesis of Indoes: Selenium–Catalyzed Reductive N–Heterocyclization of 2–Nitrostyrenes with Carbon Monoxide", Tetrahedron Letters, 1999, pp. 5717–5720, vol. 40.
Adrian L. Smith, Graeme I. Stevenson, Christopher J. Swain and Jhose L. Castro, "Traceless Solid Phase Synthesis of 2,3–Disubstituted Indoles", Tetrahedron Letters 39, 1998, pp. 8317–8320.
Kumiko Takeuchi, Jolie A. Bastian Donetta S. Gifford–Moore, Richard W. Harper, Shawn C. Miller, Jeffrey T. Mullaney, Daniel J. Sall, Gerald F. Smith, Minsheng Zhang and Matthew J. Fisher, "1.2–Disubstituted Indole, Azaindole and Benzimidazole Derivatives Possessng Amine Moiety: A Novel Series of Thrombin Inhibitors", Bioorganic & Medicinal Chemistry Letters 10, 2000, pp. 2347–2351.
Han–Cheng Zhang, Hong Ye, Allesandro F. Moretto, Kimberly K. Brumfield, and Bruce E. Maryanoff, "Facile Solid–Phase Construction of Indole Derivatives Based on a Traceless, Activating Sulfonyl Linker", Organic Letters, 2000, pp. 89–92, vol. 2, No. 1.
Han–Cheng Zhang, Kimberly K. Brumfield, Libuse Jaroskova and Bruce E. Maryanoff, "Facile Substitution of Resin–Bound Indoles via the Mannich Reaction", Tetrahedron Letters 39, 1998, pp. 4449–4452.
PCT International Search Report—International Application No. PCT/US 01/10320—Earliest Priority Date Mar. 31, 2000.
Agarwal, Shiv K. et al., "Synthesis and pharmacological activities of 1–(2,4–disubstituted phenoxy)–3–'NI–(N4–arylpiperazinyl) propanes and 1–(4–chlorobenzoyl)–3–substituted 6–methoxy–2–[4–'3–N1(N4phenylpiperazinyl) propoxy pheny]indoles"; Chemical Abstracts Svc, Colombus, OH, Indian J. Chem., SECT. B (1991), 30B(4) 413–416.

* cited by examiner

Primary Examiner—James O. Wilson
Assistant Examiner—Paul V. Ward

(57) ABSTRACT

The invention features pharmaceutically-active indoles and indazoles that are substituted with phenyl, methods of making them, and methods of using them.

12 Claims, No Drawings

PHENYL-SUBSTITUTED INDOLES AND INDAZOLES

CROSS-REFERENCE TO RELATED APPLICATIONS

This application claims priority from U.S. Provisional Application Ser. No. 60/194,071, filed on Mar. 31, 2000, and U.S. Provisional Application Ser. No. 60/194,071, filed on Feb. 28, 2001.

FIELD OF THE INVENTION

The invention relates to pharmaceutically-active fused heterobicyclic compounds and methods of using them to treat or prevent disorders and conditions, such as those mediated by the histamine $H_3$ receptor.

BACKGROUND

The histamine $H_3$ receptor is located as a presynaptic autoreceptor in the central nervous system and as a presynaptic heteroreceptor on serotonergic, noradrenergic, dopaminergic, and cholinergic neurons. The histamine $H_3$ receptor is also located peripherally in tissues such as vascular smooth muscle cells.

Proposed uses of histamine $H_3$ antagonists include the treatment or prevention of dementia, Alzheimer's disease (Panula et al. *Abstr. Society Neuroscience*, 1995, 21:1977), epilepsy (Yokoyama et al. *Eur. J. Pharmacol.*, 1993, 234:129), sleep/wake disorders (Lin et al., *Br. Res.*, 1990, 523, 325; Monti et al., *Eur. J. Pharmacol.*, 1991, 205, 283) including narcolepsy, insomnia, and jet lag, eating disorders (Machidori et al. *Brain Research*, 1992, 590:180), motion sickness, vertigo, attention deficit hyperactivity disorder, learning and memory disorders (Barnes et al. *Abstr. Society Neuroscience*, 1993, 19:1813), schizophrenia (Schlicker et al. *Naunyn Schmiedeberg's Arch. Pharmacol.*, 1996, 353:325), and sequelae associated with post-ischemic reperfusion and hypertension. (Imamura et al., *J. Pharmacol. Expt. Ther.*, 1994, 271, 1259). $H_3$ antagonists are also useful to treat or prevent neurogenic inflammation such as migraine (McLeod et al., *Abstr. Society Neuroscience*, 1996, 22, 2010), asthma (Ichinose et al., *Eur. J. Pharmacol.*, 989, 174, 49), obesity, allergic rhinitis, substance abuse, bipolar disorders, manic disorders, and depression. Histamine $H_3$ antagonists alone or in combination with a histamine $H_1$ antagonist are believed to be useful in the treatment of upper airway allergic response or allergic rhinitis (U.S. Pat. Nos. 5,217,986, 5,352,707, and 5,869,479).

As noted, the prior art related to histamine $H_3$ ligands was comprehensively reviewed recently ("*The Histamine $H_3$ Receptor-A Target for New Drugs*", Leurs, R., and Timmerman, H., (Editors), Elsevier, 1998). Within this reference the medicinal chemistry of histamine $H_3$ agonists and antagonists was reviewed (see Krause et al. and Phillips et al., respectively). Thus the importance of an imidazole moiety containing only a single substitution in the 4 position was noted together with the deleterious effects of additional substitution on activity. Particularly methylation of the imidazole ring at any of the remaining unsubstituted positions was reported to strongly decrease activity.

More recently several publications have described histamine $H_3$ ligands that do not contain an imidazole moiety. Examples include Ganellin et al *Arch. Pharm. (Weinheim, Ger.)* 1998, 331, 395; Walczynski et al *Arch. Pharm. (Weinheim, Ger.)* 1999, 332, 389; Walczynski et al Farmaco 1999, 684; Linney et al *J. Med. Chem.* 2000, 2362; U.S. Pat. No. 5,352,707; PCT Application WO99/42458, published Aug. 26, 1999; and European Patent Application 0978512, published on Feb. 9, 2000.

SUMMARY OF THE INVENTION

The invention features phenyl-substituted indole and indazole compounds, methods of making them, and methods of using them. One aspect of the invention provides compounds of the following formula (I)(B):

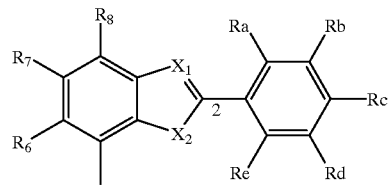

wherein $X_1$ is $CR_1$, wherein $R_1$ is H, halo, cyano, amino, or nitro; and $X_2$ is $NR_3$;

$R_3$ is H, $-SO_2$ ($C_{1-6}$alkyl), $-SO_2$ phenyl, $(C=O)(C_{1-6}$ alkyl), or $-W'Z'$;

$W'$ is a covalent bond, $(C=O)$, $SO_2$, or $C_{1-6}$ alkyl;

$Z'$ is $C_{1-6}$ alkyl, $C_{1-6}$ alkoxy, $C_{3-8}$ cycloalkyl, phenyl, or $C_{2-6}$ heterocyclic radical, optionally including in the ring up to 3 additional heteroatoms or moieties independently selected from O, N, NH, S, SO, and $SO_2$; or $Z'$ is $NR_{13}R_{14}$ where each of $R_{13}$ and $R_{14}$ is independently selected from $C_{1-6}$ alkyl, $C_{2-6}$ alkenyl, phenyl, benzyl, $C_{3-8}$ cycloalkyl, and $C_{2-5}$ heterocyclic radical;

each of $R_5$, $R_6$, $R_7$ and $R_8$ is independently H, $C_{1-6}$ alkyl, $C_{1-6}$ alkoxy, halo, nitro, or amino;

one of $R_a$, $R_b$, $R_c$, $R_d$, and $R_e$ is WZ and the others are independently selected from H, $C_{1-6}$ alkyl, $C_{1-6}$ alkoxy, halo, nitro, and amino;

W is $-O-$, $R_9$, $O-R_9$, $NR_{10}$, $-(CO)(O)R_9$, $-O(CO)R_9$, $-(CO)NR_{10}$, or $-N(R_{10})-CO-R_9$, wherein $R_9$ is $C_{1-6}$ alkylene, $C_{2-6}$ alkynylene, $C_{2-6}$ alkenylene, phenylene, or $C_{2-5}$ heterocyclic bivalent radical, and $R_{10}$ is H, $C_{1-6}$ alkyl, $C_{2-6}$ alkynyl, $C_{2-6}$ alkenyl, phenyl, or $C_{2-5}$ heterocyclic radical;

Z is $C_{2-6}$ heterocyclic radical with at least one basic nitrogen atom in the ring, optionally including in the ring up to 3 additional heteroatoms or moieties independently selected from O, $C=O$, N, NH, NG, S, SO, and $SO_2$, wherein G is $R_{15}$, $COR_{15}$, $COOR_{15}$, $SO_2R_{15}$, $SO_2N$, $CSR_{15}$; or Z is $NR_{11}R_{12}$where each of $R_{11}$ and $R_{12}$ is independently selected from H, $C_{1-6}$ alkyl, phenyl, benzyl, $C_{3-8}$ cycloalkyl, and $C_{2-5}$ heterocyclic radical; or $NR_{11}R_{12}$ taken together is a $C_{6-8}$ cycloalkylimino radical; and $R_{15}$ is $C_{1-6}$ alkyl, $C_{2-6}$ alkynyl, $C_{2-8}$ alkenyl, $C_{3-7}$ cycloalkyl, and $C_{4-7}$ cycloalkenyl;

each of the above hydrocarbyl or heterocyclic groups being optionally substituted with between 1 and 3 substituents selected from $C_{1-3}$ alkyl, $C_{1-3}$ alkoxy, halo, hydroxy, phenyl, and phenyl($C_{1-3}$ alkyl); and wherein each of the above heterocyclic groups may be attached to the rest of the molecule by a carbon atom or a heteroatom;

or a pharmaceutically acceptable salt, amide, ester, or hydrate thereof.

According to another aspect of the invention, the disclosed compounds and certain other compounds, are useful for the treatment and/or prevention of diseases and conditions mediated by the histamine 3 ($H_3$) receptor.

A third aspect of the invention features methods of making the disclosed compounds.

Additional features of the invention are disclosed in the following description and examples, and in the appended claims.

DETAILED DESCRIPTION

The invention features pharmaceutically active phenyl-substituted indoles and indazoles and methods of making and using them. The description is organized as follows:

A. Terms

B. Compounds

C. Synthetic Methods

D. Uses (including dosages, formulations, and related compounds)

E. Synthetic Examples

F. Biological Examples

G. Other Embodiments

H. Claims

A. Terms

The following terms are defined below and by their usage throughout this disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl does not include cycloalkenyl.

"Alkynyl" include straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

"Aryl" includes phenyl, naphthyl, biphenylyl, and so on.

"Cycloalkyl" includes cyclopropyl, cyclobutyl, cyclopentyl, cyclohexyl, cycloheptyl, cyclooctyl, and so on.

"Cycloalkenyl" includes cyclobutenyl, cyclobutadienyl, cyclopentenyl, cyclopentadienyl, cyclohexenyl, cyclohexadienyl, cyclohexatrienyl (phenyl), cycloheptenyl, and so on. "Cycloalkynyl" includes the analogous rings with one or more triple bonds.

"Heterocyclic radicals" include aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Examples of heterocyclic radicals include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclic radicals for Z include morpholinyl, piperazinyl, pyrazinyl, pyrrolidinyl, pyridyl, cyclohexylimino, cycloheptylimino,and more preferably, piperidyl.

"halo" includes fluoro, chloro, bromo, and iodo, and preferably fluoro or chloro.

"patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"composition" includes a product comprising the specified ingredients in the specified amounts as well as any product which results directly or indirectly from combinations of the specified ingredients in the specified amounts.

Concerning the various radicals in this disclosure and in the claims, two general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is W in formula (I)(B) which links Z with the phenyl group (-Ph-WZ). Subject to the claims, W can be an alkyl (strictly, alkylene) group (-Ph-$CH_2CH_2CH_2$-Z), an aminoalkyl group (—Ph-NH—$CH_2CH_2CH_2$-Z), an alkoxy group (-Ph-O—$CH_2CH_2CH_2$-Z), an "oxa" (—Ph-O-Z), and so on.

Second, radicals or structure fragments as defined herein are understood to include substituted radicals or structure fragments. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, and 3-iodocyclopentyl), hydroxyalkyl, aminoalkyl, nitroalkyl, alkylalkyl, and so on.

Preferred substitutions for phenyl include methyl, methoxy, fluoromethyl, difluoromethyl, perfluoromethyl (trifluoromethyl), 1-fluoroethyl, 2-fluoroethyl, ethoxy, fluoro, chloro, and bromo, and particularly methyl, fluoromethyl, perfluoro, methoxy, and fluoro.

Examples of other substituted radicals or fragments include 1-methyl-2-pyrrolidino, 4-(piperidyl)-piperidyl, [4-(N-benzyl)piperidyl]amino, 4-fluorobenzylamino, beta-hydroxyethoxy, beta-hydroxypropoxy, 2-oxo-pyrrolidino, 4-(1-methyl-4-piperidinyl), 4-(5-methyl-thiazoyl), 4-chlorobenzyl, 4-fluorobenzyl, 4-methylbenzyl, 4-methylpiperazinyl, piperazinyl, and 4-(1-isopropyl-4-piperidinyl).

B. Compounds

One aspect of the invention features compounds of formula (I)B as described in the Summary section above. The invention encompasses the described compounds and pharmaceutically acceptable salts, estes, amides, and hydrates thereof.

Preferred compounds include those compounds of formula (I)B wherein: (a) $R_3$ is H or $C_{1-3}$ alkyl; (b) $R_3$ is —(C=O)$C_{1-6}$ alkyl; (c) $R_3$ is —SO$_2$($C_{1-3}$ alkyl); (d) $R_3$ is methylsulfonyl; (e) W' is a covalent bond; (f) W' is SO$_2$ or (C=O); (g) $R_c$ is WZ; (h) $R_b$ or $R_d$ is WZ; (i) W is ethoxy, propoxy, or butoxy; (j) W is —O—; (k) one of $R_b$, $R_c$, and $R_e$ is WZ and the others are independently selected from H, methyl, ethyl, methoxy, ethoxy, amino, nitro, and halo; and $R_a$ and $R_d$ are each independently H or methyl; (I) at least two of the following apply: $R_c$ is WZ; W is propoxy or ethoxy; and Z is N-piperidino, 2-(N-methyl)pyrrolidino, or N,N-dimethyl; or combinations thereof.

Additional preferred compounds include those wherein (m) Z is piperazino or N-methylpiperazino, and more preferably Z is pyrrolidino, N-methyl-pyrrolidino, pyridyl, thiazoyl, piperidino, or $NR_{11}R_{12}$ where each of $R_{11}$ and $R_{12}$ is independently selected from H, $C_{1-6}$ alkyl, phenyl, benzyl, $C_{3-6}$ cycloalkyl, and $C_{2-5}$ heterocyclic radical or taken together with the N form a $C_{6-8}$ cycloalkylamino radical; or wherein (m) is combined with (a) through (l) above.

Further preferred compounds include those wherein (n) one of $R_b$, $R_c$, and $R_e$ is WZ and the others are independently selected from H, methyl, ethyl, methoxy, ethoxy, amino, and halo; and $R_a$ and $R_d$ are each independently H or methyl; W is —O— or $C_{1-3}$ alkoxy; Z is piperazino or N-methylpiperazino, and more preferably pyrrolidino, N-methylpyrrolidino, pyridyl, thiazoyl, piperidino, or $NR_{11}R_{12}$ where each of $R_{11}$ and $R_{12}$ is independently selected from H, $C_{1-2}$ alkyl, phenyl, benzyl, $C_{3-8}$ cycloalkyl, and $C_{2-5}$ heterocyclic radical; each of $R_6$ and $R_7$ are each independently H, methyl, methoxy, or ethoxy; and each of $R_5$ and $R_8$ is H. Preferred compounds also include those wherein for example one or more of (a) through (n) is combined with (o) $R_3$ is H or —SO$_2$ ($C_{1-6}$ alkyl); or (p) $R_3$ is SO$_2$(phenyl) and (C=O)($C_{1-6}$ alkyl).

Examples of more preferred compounds include: (i) 2-[4-[2-[1-(methyl)-2-pyrrolidinyl]ethoxy]phenyl)-1H-indole; 2-[4-[2-[1-(methyl)-2-pyrrolidinyl]ethoxy]phenyl)-1-(methylsulfonyl)-1H-indole; 2-[4-[3-Piperidinopropoxy]phenyl)-1H-indole; 2-[4-[3-Piperidinopropoxy]phenyl)-1-(methylsulfonyl)-1H-indole; and 2-[3-[3-Piperidinopropoxy]phenyl)-1-(methylsulfonyl)-1H-indole; and (ii) 2-(4-(3-(4-methylpiperazino)propoxy)-phenyl)indole; and 1-(methylsulfonyl)-2-(4-(3-(4-methylpiperazino)-propoxy)phenyl)indole.

Other examples of compounds, and methods of making them, are provided in the next section.

C. Synthetic Chemical Methods

The invention provides methods of making the disclosed compounds according to traditional organic synthetic methods as well as matrix or combinatorial synthetic methods. Schemes 1 through 9 describe suggested synthetic routes.

Using these Schemes, the guidelines below, and the examples in section E, a person of skill in the art may develop analogous or similar methods for a given compound.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Examples of the described synthetic routes includes Synthetic Examples 1 through 17. Compounds analogous to the target compounds of these examples can be, and in many cases, have been, made according to similar routes. The disclosed compounds are useful in basic research and as pharmaceutical agents as described in the next section.

Scheme 1

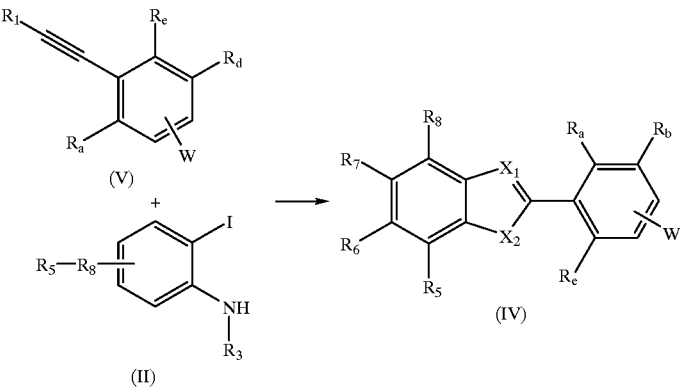

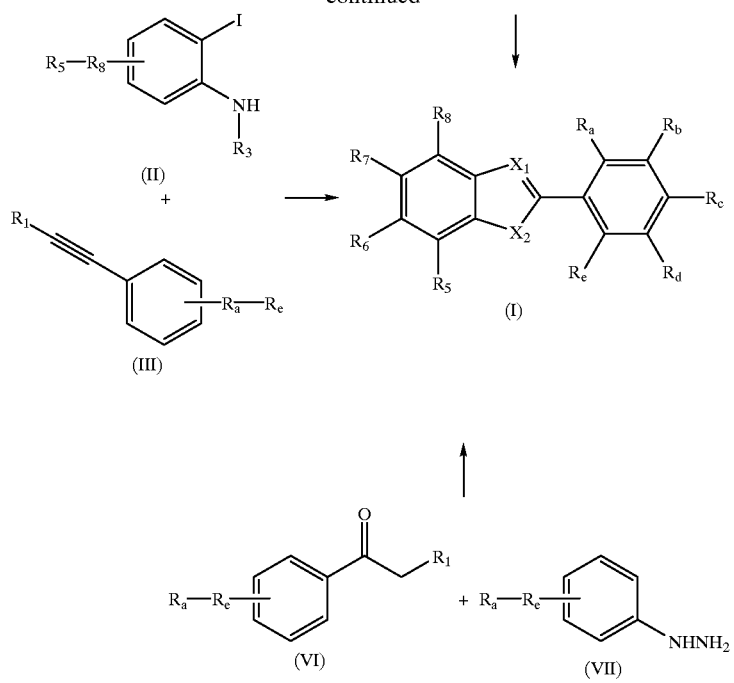

Generally, a compound of formula (V), a known compound or compound prepared by known methods, is reacted with a compound of formula (II), a known compound or compound prepared by known methods, in the presence of a palladium catalyst such as dichlorobis(triphenylphosphine) palladium, and CuI, or the like, in the presence of a base such as triethylamine, or the like, in a solvent such as DMF, THF, DMA, and the like, to yield the corresponding compound of formula (IV). Compound (IV) is then further reacted, as outlined in Schemes 5–7 below, to form the compound of formula (I). Alternatively a compound of formula (III) can be reacted with a compound of formula (II) using the above described, or similar methods to form a compound of formula (I) directly. In addition compounds of formula (I), in which $X_2$ is NH can be obtained by reacting a compound of formula (VI) with an aromatic hydrazine of formula (VII) in the presence of a strong acid such as PPA.

Compounds of formula (II) wherein $R_3$ is chosen from either —$SO_2(C_{1-6}$ alkyl), —$SO_2$ phenyl, (C=O)($C_{1-6}$ alkyl), and $R_5$–$R_8$ are selected from H, $C_{1-6}$ alkyl, $C_{1-6}$ alkoxy, halo, nitro, may be prepared according to the process outlined in Scheme 2.

Scheme 2

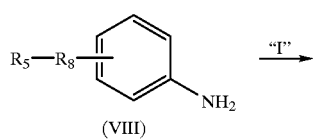

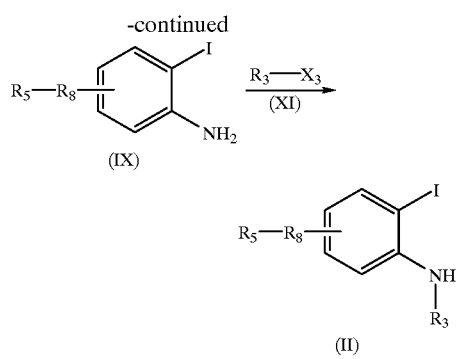

A compound of formula (VIII), wherein $R_5$–$R_8$ are selected from H, $C_{1-5}$ alkyl, $C_{1-6}$ alkoxy, halo, nitro, a known compound or compound prepared by known methods, is treated with an iodinating agent such as N-iodo succinamide, ICl, or $I_2$ in a solvent such as acetic acid, acetonitrile, or the like, to yield the corresponding compound of formula (IX). The compound (IX), a known compound or compound prepared by known methods, is reacted with a compound of formula (XI), in which $R_3$ is chosen from either —$SO_2(C_{1-6}$ alkyl), —$SO_2$phenyl, (C=O)($C_{1-6}$ alkyl), (C=O)($C_{1-6}$ alkoxy), (C=O)phenyl, and $X_3$ is selected from Br, Cl, F, or a conventional activating anhydride, or ester, in the presence of a base such as pyridine, N,N-dimethyl aminopyridine, triethylamine, or sodium hydroxide in an organic solvent such as DCM, THF, or DMF to yield the corresponding compound of formula (II).

Compounds of formula (V) wherein W is OH, $NH_2$, $CO_2H$, and $R_a$–$R_e$ are selected from H, $C_{1-6}$ alkyl, $C_{1-6}$ alkoxy, halo, or nitro may be prepared according to the processes outlined in Scheme 3.

Scheme 3

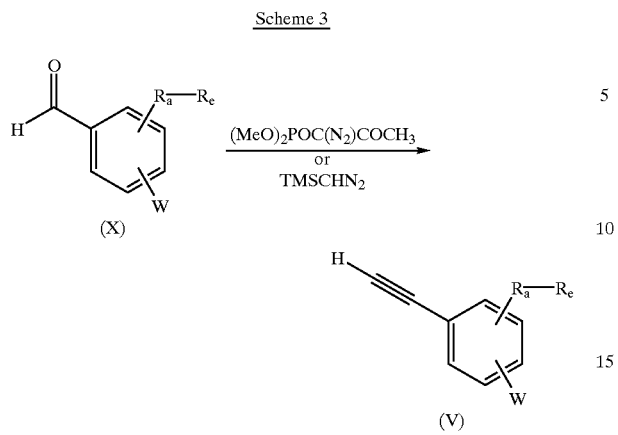

Scheme 5

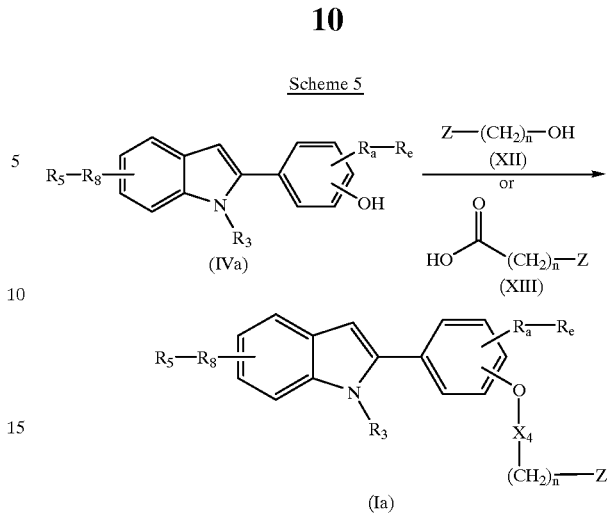

A compound of formula (X) wherein W is OH, $NH_2$, $CO_2H$, and $R_a-R_e$ are selected from H, $C_{1-6}$ alkyl, $C_{1-6}$ alkoxy, halo, or nitro, is reacted with a diazophosphonate in the presence of a base such as, $K_2CO_3$, KOH, or DBU, in a solvent such as MeOH, EtOH, or DMF, to yield compounds of formula (V). Alternately compounds of formula (V) can also be prepared by treating a compound of formula (X) with trimethylsilyldiazomethane, in the presence of a strong base such as LDA or LHMDS, in a solvent such as, THF, Ether, or MTBE, to yield compounds of formula (V). In addition compounds of formula (V) may also be obtained using methods known to one skilled in the art as outlined in R. C. Larock "Comprehensive Organic Transformations", VCH Publishers, 1989, p. 295–296.

Specifically compounds of formula (IV) wherein W is —OH, —$NH_2$, —C(O)OH may be prepared according to the processes outlined in Scheme 4.

Scheme 4

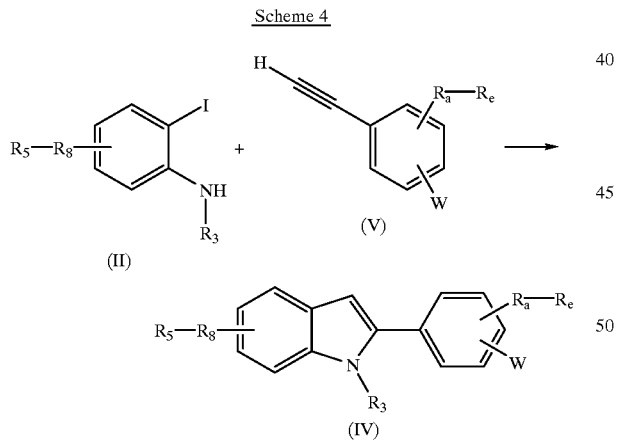

Specifically, Compounds of formula (II), as defined in Scheme 2, are combined with compounds of formula (V), as defined in Scheme 3, in the presence of a palladium catalyst such as, $Pd(PPh_3)_2Cl_2$, or $Pd(OAc)_2$, and a copper source such as CuI, CuOAc, or CuBr, and a base such as triethylamine or pyridine, in a solvent such as THF or DMF, to provide the corresponding compounds of formula (IV).

Compounds of formula (I) in which n is a whole number between 0 and 4, and Z is as described in claim (1), and $R_5-R_8$ and $R_a-R_e$ are as described in Scheme 4, can be obtained by the procedures described in Scheme 5–7.

Specifically a compound of formula (IVa) wherein $R_3$, $R_a-R_e$ and $R_5-R_8$ are as described in Scheme 4, is reacted with an alcohol of formula (XII), wherein Z is as described in claim (1), and n is a whole number between 0 and 4, in the presence of a phosphine such as triphenyl phosphine, polymer supported triphenylphosphine, or tributylphosphine, and an azodicarboxylate such as diisopropylazodicarboxylate, 1,1'-(azodicarbonyl) dipiperidine, or other Mitsunobu conditions, in a solvent such as DCM or THF, to afford the corresponding compounds of formula (I) in which $X_4$ is a covalent bond, and n is a whole number between 0 and 4.

Alternatively compounds of formula (IV) as described above, can be reacted with carboxylic acids of formula (XIII), in which Z is defined as above, and n is a whole number between 0 and 3, in the presence of an activating agent such as carbonyldiimidazole or thionyl chloride, with a base such as N-methyl morpholine, triethylamine, or N,N-dimethyl-4-aminopyridine to yield the corresponding compound of formula (I), in which $X_4$ is defined as a carbonyl group.

Alternatively compounds of formula (Ib) can be obtained by the methods described in Scheme 6.

Scheme 6

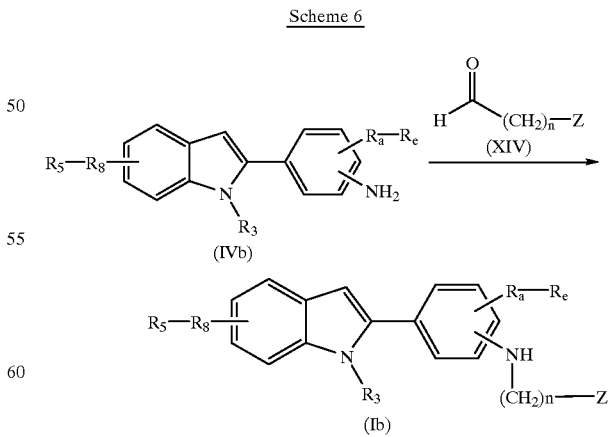

Specifically, a compound of formula (IVb) in which $R_3$, $R_5-R_8$ and $R_a-R_e$ is as defined in scheme 4, is reacted with an aldehyde of formula (XIV) in which n is a whole number between 0 and 3, and Z is as described in claim (1), in the presence of a reducing agent such as NaBH$_3$(CN) or NaBH(OAc)$_3$, in a solvent such as MeOH or THF, to afford the corresponding compound of formula (I).

Alternatively, compounds of formula (Ic) can be obtained using the methods outlined in Scheme 7.

Scheme 7

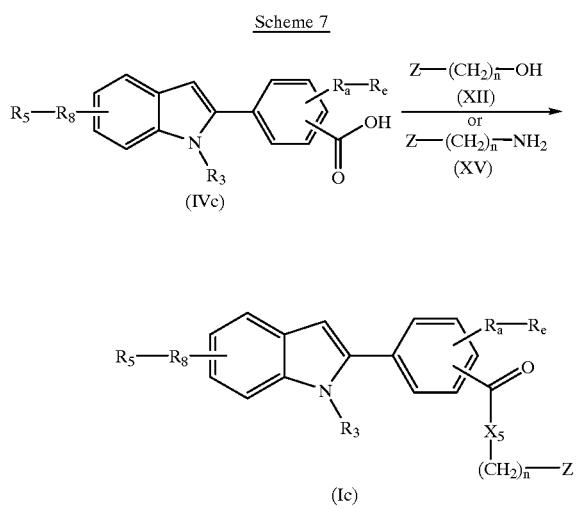

(IVc)

(Ic)

Specifically, a compound of formula (IVc) in which $R_3$, $R_5$–$R_8$, and $R_a$–$R_e$ is defined as in Scheme 4, is reacted with an alcohol of formula (XII), or an amine of formula (XV), in which Z is as defined in claim (1), and n is a whole number between 0 and 4, in the presence of an activating agent such as carbonyldiimidazole or thionyl chloride, with a base such as N-methyl morpholine, triethylamine, or N,N-dimethyl-4-aminopyridine to yield the corresponding compound of formula (I), in which X$_5$, is defined as O or NH.

In addition, compounds of formula (I)B can be converted to other compounds of formula (I)B as defined in Scheme 8 below.

with; a nitrating agent such as HNO$_3$ or an electrophilic halogenating agent such as Br$_2$ or NIS, using solvents and conditions known to one skilled in the art, to yield the corresponding compound of formula (If) in which R$_1$ is defined as NO$_2$, Br, Cl, or I. Additionally a compound of formula (If) in which R$_1$ is NO$_2$ can be further elaborated through reduction with an appropriate reducing agent such as SnCl$_2$ or iron metal, to yield the corresponding compound of formula (Ie), in which R$_1$ is NH$_2$.

Additionally, compounds of formula (Ie) in which R$_3$ is defined as in Scheme 2, and R$_5$–R$_8$, and R$_a$–R$_e$ are as described in Scheme 4, can be treated with a strong base such as KOH, K$_2$CO$_3$, or the like, in a solvent such as THF, MeOH, or the like, to yield the corresponding compounds of formula (If).

In addition, compounds of formula (If) can be converted to compounds of the corresponding formula (Ie) by treatment with a strong base such as n-BuLi, NaH, or the like, and an alkylating or acylating agent of formula (XI), wherein R$_3$ and X$_3$ are as defined in Scheme 2.

The synthesis of compounds of formula (III) in which R$_a$–R$_e$ are as defined in Scheme 3, R$_{11}$, and R$_{12}$ are as defined claim (1), and n is an integer from 2 to 5, and compounds of formula (IV) in which the above definitions apply, and R$_{13}$ is C$_{1-6}$ alkyl are described in Scheme 9.

Scheme 9

(XVI)

(XVII)

Scheme 8

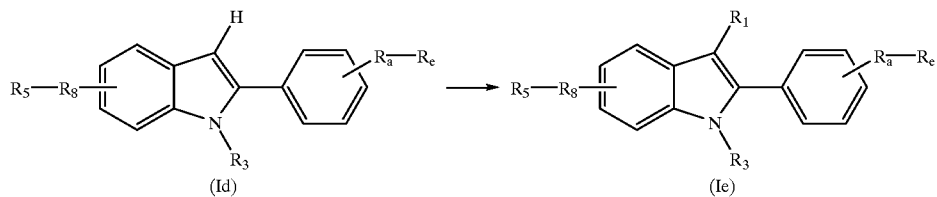

(Id)

(Ie)

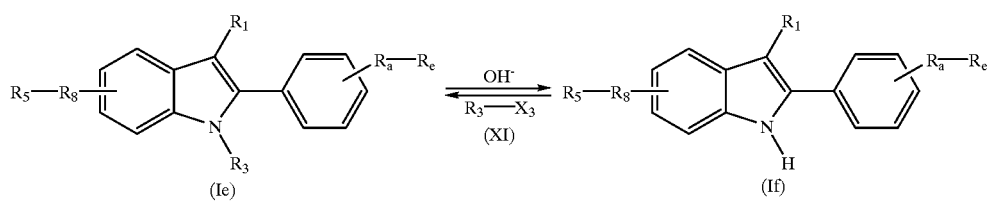

(Ie)

(If)

Specifically, a compound of formula (Id) in which R$_3$, R$_5$–R$_8$, and R$_a$–R$_e$ are as described in Scheme 4, is treated

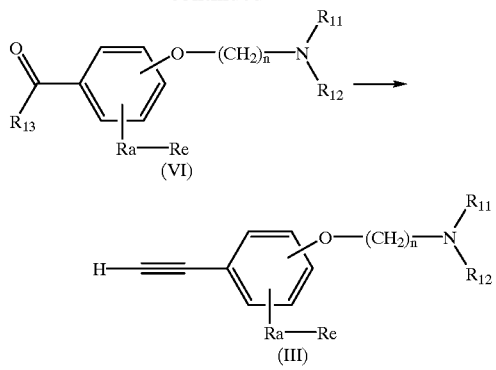

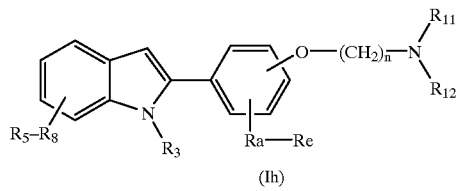

Specifically, a compound of formula (XVI) in which $R_{13}$ is H, or $C_{1-6}$ alkyl, and $R_a$–$R_e$ is as previously described, is treated with a base such as NaH or $K_2CO_3$, and a compound of formula (XVIII), in which $X_6$ is selected from Cl, Br, I, —$OSO_2CH_3$, —OTs, or OTf, and $X_7$ is selected from the same definition as $X_6$ but less reactive than the element chosen for $X_6$, and n is an integer from 2 to 5, in a solvent such as THF, DMF or DMSO, to yield the corresponding compound of formula (XVII). The compound of formula (XVII) is then treated with a compound of formula (XIX), wherein $R_{11}$ and $R_{12}$ are as defined in claim (1), in a solvent such as DMF or DCM, to afford the corresponding compound of formula (VI).

Compounds of formula (III) are prepared by treatment of corresponding compounds of formula (IV), in which $R_{13}$ is defined as H, with a base such as LDA or LIHMDS, and $TMSCHN_2$, in a solvent such as THF, diethylether, or the like. Alternately, compounds of formula (III) can also be prepared by treating corresponding compounds of formula (IV), with a base such as $K_2CO_3$ or KOH, and a phosphonate such as $(CH_3O)_2P(O)C(N_2)C(O)CH_3$, in a solvent such as MeOH.

Compounds of formula (Ig) can be obtained using the methods described in Scheme 10.

Scheme 10

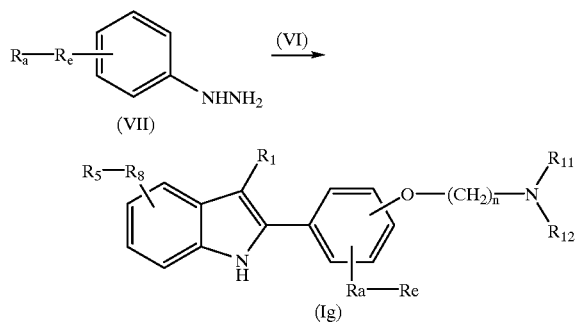

Specifically a compound of formula (VI) as defined in scheme 9 is treated with an aryl hydrazine of formula (VII), wherein $R_5$–$R_8$ is as defined as in claim (1), in polyphosphoric acid, to yield the corresponding compound of formula (Ig).

Additionally compounds of formula (I) can be formed using the procedures outlined in Scheme 11.

Specifically a compound of formula (II), as defined in Scheme 2 is combined with a compound of formula (III) as defined in Scheme 9, in the presence of a palladium catalyst such as $Pd(PPh_3)_2Cl_2$ or $Pd(OAc)_2$, and a copper source such as CuI, CuOAc or CuBr, and a base such as triethylamine or pyridine, in a solvent such as THF or DMF, to provide the corresponding compounds of formula (Ih).

D. Uses

According to the invention, the disclosed compounds and compositions are useful for the amelioration of symptoms associated with, the treatment of, and/or the prevention of, the following conditions and diseases, or symptoms associated with them: dementia, Alzheimer's disease, narcolepsy, eating disorders, motion sickness, vertigo, attention deficit hyperactivity disorder, learning and memory disorders, schizophrenia, mild cognitive impairment upper airway allergic response (allergic rhinitis), insomnia, jet lag, obesity, asthma, neurogenic inflammation, substance abuse, bipolar disorders, manic disorders, and depression. The invention also features pharmaceutical compositions, which include, without limitation, one or more of the disclosed compounds, and a pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the use of other medications. An effective amount means that amount of pharmaceutical reagent (such as a prodrug, metabolic precursor, or active compound) that elicits the biological or medical response desired. In general, a therapeutically effective amount will be between 0.01 and 1000 mg/kg per day, preferably between 0.01 and 250 mg/kg body weight, and daily dosages will be between 0.50 and 5000 mg for an adult subject of normal weight. Capsules, tablets or other formulations (such as liquids and film-coated tablets) may be of between 0.20 and 100 mg, such as 0.20, 0.50, 1.0, 2.0, 3.0, and 10 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray) as appropriate depending on the overall health and condition of the patient as determined by a physician or veterinary doctor.

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The present invention also provides compositions and methods useful for the treatment of disorders or conditions modulated, preferably antagonized, by the histamine $H_3$ receptor in combination with compounds that modulate other receptors including, but not limited to, histamine $H_1$ and histamine $H_2$ receptors. The present invention includes compounds and compositions useful in methods of combination therapy for the treatment of diseases or conditions modulated by the histamine $H_3$ receptor in combination with compounds that are selective serotonin re-uptake inhibitors (SSRIs), such as PROZAC™, or are selective norepinephrine uptake inhibitors. Such combination methods include (a) administering the two or more pharmaceutical agents separately formulated and at separate times, and (b) administering the two or more agents simultaneously in a single formulation or in separate formulations administered more or less at the same time. For example, one aspect is a method of treatment comprising administering at least one histamine $H_3$ receptor modulating compound disclosed herein and administering at least one compound selected from a histamine $H_1$ receptor modulating compound, a histamine $H_2$ receptor modulating compound, a selective serotonin reuptake inhibitor (such as PROZAC™), or a selective norepinephrine uptake inhibiting compound.

4. Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19 which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9- phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate).

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups
Examples of special NH protective groups include
N-Alkyl and N-Aryl Amines
N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carboxyl Group

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

E. CHEMICAL EXAMPLES

Example 1

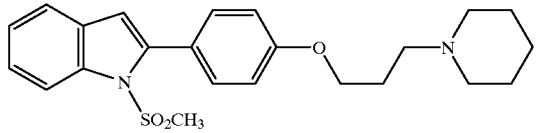

2-[4-[3-Piperidinopropoxy]phenyl]-1-(methylsulfonyl)-1H-indole $K_i=7$ nM

Step A Preparation of 2-iodo-N-(methanesulfonyl)aniline

Methanesulfonyl chloride (4.4 mL, 57 mmol) was added to a 0° C. dichloromethane (200 mL) solution containing 2-iodoaniline (5.0 g, 23 mmol) and triethylamine (9.6 mL, 69 mmol). The resulting mixture was stirred for 90 minutes, washed with HCl (0.5 M). The organics were separated then dried over sodium sulfate and concentrated in vacuo. The residue was then treated with potassium hydroxide (2.0 M in 1:1 methanol:water, 75 mL) for 30 min. This material was then diluted with dichloromethane and washed with HCl (1.0 N, 300 mL). The organics were separated then dried over sodium sulfate and concentrated to provide the title compound (5.15 g) as a tan solid.

Step B Preparation of 4-(methoxyethoxymethyl) benzaldehyde

Sodium hydride (2.4 g (60%), 60 mmol) was added to 4-hydroxybenzaldehyde (6.0 g, 50 mmol) in N,N-dimethylformamide (100 mL). The suspension was stirred for 1 hour and then treated with 2-methoxyethoxymethyl chloride (6.8 mL, 60 mmol), and allowed to stir an additional 16 hours. The reaction was then partitioned between water and ether:ethyl acetate (1:1). The organics were then washed with water (4×), dried (potassium carbonate), and concentrated. The crude materials were then purified by silica gel chromatography (hexanes:ethyl acetate) to afford the title compound (9.0 g).

Step C Preparation of 1-ethynyl-4-(methoxyethoxymethyl) benzene

Dimethyl[(2-diazo-3-oxo)propyl] phosphonate was added in 4 portions to a suspension of potassium carbonate (4.96 g, 36 mmol), the product of Step B (3.78 g, 18 mmol), and methanol (50 mL). The reaction was stirred for 16 hours. and concentrated in vacuo. The residue was taken up in ether, washed with water (3×), dried (potassium carbonate), and concentrated. The crude product was purified by silica gel chromatography (hexane:ethyl acetate) to provide the title compound (2.3 g).

Step D Preparation of 2-(4-(methoxyethoxymethyl)phenyl)-1-(methanesulfonyl)indole The products of Step A (3.0 g, 10 mmol) and step C (2.2 g, 10 mmol) were combined in N, N-dimethylformamide (20 mL) and triethylamine (5 mL). The solution was then treated with dichlorobis(triphenylphosphine)palladium(II) (0.7 g, 1.0 mmol), copper(l)iodide (380 mg, 2.0 mmol), and stirred at 80° C. for 17 hours. The reaction was then diluted with ether:ethyl acetate (1:1, 200 mL), washed with water (5×), dried (potassium carbonate), and concentrated in vacuo. The crude material was then purified by silica gel chromatography (hexane:ethyl acetate) to afford the title compound (3.36 g).

Step E Preparation of 2-(4-hydroxyphenyl)-1-(methanesulfonyl)-indole

A solution of the product of Step D (1.5 g, 4.0 mmol) in methanol (10 mL) was treated with HCl (10 mL, 4 N in dioxane). The reaction was allowed to stir for 2 hr, concentrated, and purified by silica gel chromatography (methanol:dichloromethane), to afford the title compound (0.93 g).

Step F Preparation of 2-[4-[3-piperidinopropoxy]phenyl]-1-(methanesulfonyl)indole A mixture of immobilized triphenylphosphine resin (330 mg, 1.0 meq (Fluka)), and the product of Step E (140 mg, 0.50 mmol) in tetrahydrofuran (6.0 mL) was treated with 3-(piperdin-1-yl)propanol (143 mg, 1.0 mmol) followed by diethylazidodicarboxylate (0.16 mL, 1.1 mmol). The reaction was shaken for 20 hr. and filtered. The filtrate was concentrated in vacuo and the residue purified by silica gel chromatography (methanol/ethyl acetate) to afford pure title compound (97 mg). MS (ESI) m/z 413 (MH$^+$); $^1$H-NMR (CDCl$_3$) δ 8.13 (d, 1H), 7.59 (d, 1H), 7.50 (d, 2H), 7.36 (m, 2H), 6.97 (d, 2H), 6.68 (s, 1H), 4.08 (t, 2H), 2.72 (s, 3H), 2.4 (m, 6H), 1.63 (m, 6H), 1.45 (m, 2H).

Example 2

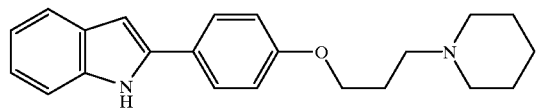

2-[4-(3-Piperidinopropoxy]phenyl)-1H-indole $K_i$= 48nM

A solution of the product from Step F, Example 1 (41.4 mg, 0.10 mmol) in methanol (2.0 mL) was treated with potassium hydroxide (1.0 mL, 40% aq). The reaction was stirred at 40° C. for 48 hours and concentrated in vacuo. The residue was purified by silica gel chromatography (methanol:dichloromethane) to provide pure title compound (3.7 mg). MS (ESI) m/z 335 (MH$^+$); $^1$H-NMR (CDCl$_3$) δ 8.19 (bs, 1H), 7.48 (d, 2H), 7.27 (m, 2H), 7.07 (t, 1H), 7.00 (t, 1H), 6.86 (d, 2H), 6.61 (s, 1H), 3.96 (t, 2H), 2.5 (m, 6H), 1.4 (m, 8H).

Example 3

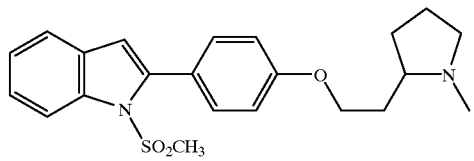

2-[4-[2-[1-(methyl)-2-pyrrolidinyl]ethoxy]phenyl)-1-(methylsulfonyl)-1H-indole $K_i$=77 nM The title compound was obtained (70 mg) by the same general method as Example 1 by substituting 2-ethoxy-1-methylpyrrolidine for 3-(piperdin-1-yl)propanol in step F. MS (ESI) m/z 399 (MH$^+$); $^1$H-NMR (CDCl$_3$) δ 8.13 (d, 1H), 7.60 (d, 1H), 7.50 (2, 2H), 7.37 (m, 2H), 6.97 (d, 2H), 6.68 (s, 1H), 4.08 (m, 2H), 3.12 (m, 1H), 2.72 (s, 3H), 2.39 (s, 3H), 2.1–1.7 (m, 8H).

Example 4

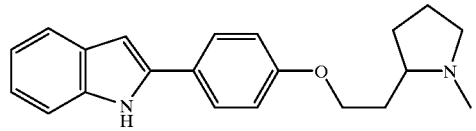

2-[4-[2-[1-(methyl)-2-pyrrolidinyl]ethoxy]phenyl)-1H-indole $K_i$=100 nM

The title compound was obtained (14.3 mg) by the same general method as Example 2 by substituting the product of Example 3 for the product of example 1 as the starting material. MS (ESI) m/z 321 (MH$^+$); $^1$H-NMR (CDCl$_3$) δ 8.15 (bs, 1H), 7.49 (d, 1H), 7.47 (d, 2H), 7.26 (d, 1H), 7.04 (t, 1H), 6.98 (t, 1H), 6.85 (d, 2H), 6.59 (s, 1H), 3.95 (m, 2H), 2.96 (t, 1H), 2.23 (s, 3H), 2.1–1.7 (m, Example 5

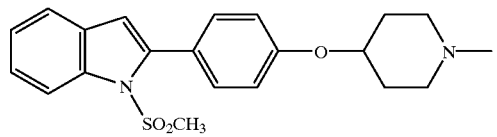

2-[4-[1-(methyl)-4-piperidinyl]oxyphenyl]-1-(methylsulfonyl)-1H-indole $K_i$=107nM The title compound was obtained (54.8 mg) by the same general method as Example 1 by substituting 4-hydroxy-1-methylpiperidine for 3-(1-piperdinyl) propanol in Step F. MS (ESI) m/z 385 (MH$^+$); $^1$H-NMR (CDCl$_3$) δ 8.13 (d, 1H), 7.59 (d, 1H), 7.50 (d, 2H), 7.37 (m, 2H), 6.96 (d, 2H), 6.68 (s, 1H), 4.41 (m, 1H), 2.76 (m, 2H), 2.73 (s, 3H), 2.34 (s, 3H), 2.07 (m, 2H), 1.92 (m, 2H), 1.78 (m, 2H).

Example 6

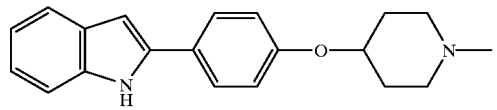

2-[4-[1-(methyl)-4-piperidinyl]oxyphenyl] 1H-indole $K_i$=390 nM

The title compound was obtained (13.8 mg) by the same general method as Example 2 by substituting the product of Example 5 for the product of example 52 as the starting material. MS (ESI) m/z 307 (MH$^+$); $^1$H-NMR (CDCl$_3$) δ 8.36 (bs, 1H), 7.63 (d, 1H), 7.60 (d, 2H), 7.41 (d, 1H), 7.19 (t, 1H), 7.13 (t, 1H), 7.00 (d, 2H), 6.73 (s, 1H), 4.42 (m, 1H), 2.76 (m, 2H), 2.40 (m, 2H), 2.36 (s, 3H), 2.09 (m, 2H), 1.92 (m, 2H).

Example 7

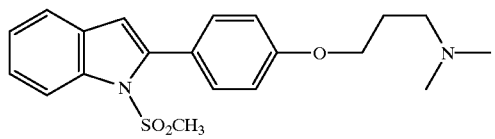

2-[4-[3-Dimethylaminopropoxy]phenyl]-1-(methylsulfonyl)-1H-indole $K_i$=120 nM

The title compound was obtained (95 mg) by the same general method as Example 1 by substituting N,N-dimethyl-3-amino-1-propanol for 3-(piperdin-1-yl) propanol in Step F. MS (ESI) m/z 373 (MH$^+$); $^1$H-NMR (CDCl$_3$) δ 8.13 (d, 1H), 7.59 (d, 1H), 7.50 (d, 2H), 7.36 (m, 2H), 6.97 (d, 2H), 6.68 (s, 1H), 4.09 (t, 2H), 2.73 (s, 3H), 2.50 (t, 2H), 2.29 (s, 6H), 2.01 (m, 2H).

Example 8

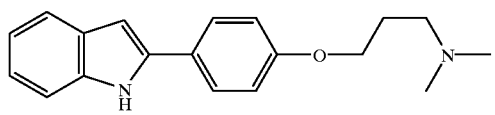

2-[4-[3-Dimethylaminopropoxy]phenyl] 1H-indole $K_i$=500 nM

The title compound was obtained (13.8 mg) by the same general method as Example 2 by substituting the product of Example 7 for the product of Example 1 as the starting material. MS (ESI) m/z 295 (MH$^+$); $^1$H-NMR (CDCl$_3$) δ 8.10 (bs, 1H), 7.62 (d, 1H), 7.60 (d, 2H), 7.40 (d, 1H), 7.19 (t, 1H), 7.13 (t, 1H), 7.00 (d, 2H), 6.72 (s, 1H), 4.09 (t, 2H), 2.50 (t, 2H), 2.29 (s, 6H), 2.01 (m, 2H).

Example 9

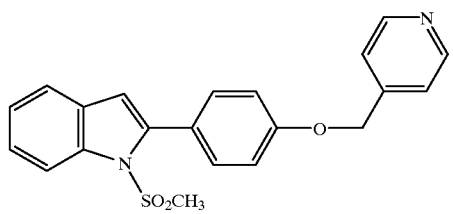

2-[4-[4-Pyridinyl]methoxyphenyl]-1-(methylsulfonyl)-1H-indole $K_i$=5000 nM

The title compound was obtained (185 mg) by the same general method as Example 1 by substituting 4-hydroxymethylpyridine for 3-(piperdin-1-yl) propanol in Step F. MS (ESI) m/z 379 (MH$^+$); $^1$H-NMR (CDCl$_3$) δ 8.67 (d, 2H), 8.13 (d, 1H), 7.60 (d, 1H), 7.54 (d, 2H), 7.41 (d, 2H), 7.38 (m. 2H), 7.03 (d, 2H), 6.69 (s, 1H), 4.77 (s, 2H), 2.74 (s, 3H).

Example 10

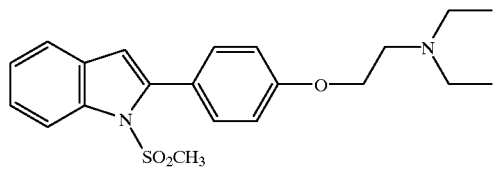

2-[4-[2-Diethylaminoethoxy]phenyl]-1-(methylsulfonyl)-1H-indole $K_i$=369 nM

The title compound was obtained (140 mg) by the same general method as Example 1 by substituting 2-(N,N-diethylamino)ethanol for 3-(piperdin-1-yl) propanol in Step F. MS (ESI) m/z 387 (MH$^+$); $^1$H-NMR (CDCl$_3$) δ 8.14 (d, 1H), 7.59 (d, 1H), 7.50 (d, 2H), 7.16 (m, 2H), 6.97 (d, 2H), 6.67 (s, 1H), 4.12 (t, 2H), 2.91 (t, 2H), 2.73 (s, 3H), 2.67 (q, 4H), 1.10 (t, 6H).

Example 11

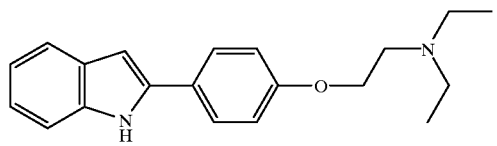

2-[4-[2-Diethylaminoethoxy]phenyl]-1H-indole $K_i$= 523 nM

The title compound from Example 10 (38.6 mg, 0.10 mmol) was treated with tetrabutyl ammonium fluoride (4.0 mL, of a 0.5 M in tetrahydrofuran) and stirred for 14 hours at 60° C. The resulting solution was concentrated in vacuo, dissolved in dichloromethane, and washed with water. The organics were then concentrated, and the crude product purified by silica gel chromatography (methanol/dichloromethane) to afford pure title compound (5.9 mg). MS (ESI) m/z 309 (MH$^+$); $^1$H-NMR (CDCl$_3$) δ 8.21 (bs, 1H), 7.53 (d, 1H), 7.51 (d, 2H), 7.31 (d, 1H), 7.09 (t, 1H), 7.04 (t, 1H), 6.90 (d, 2H), 6.64 (s, 1H), 4.06 (t, 2H), 2.88 (t, 2H), 2.63 (q, 4H), 1.04 (t, 6H).

Example 12

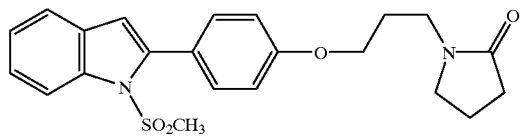

2–14-[3-(2-Oxo-pyrrolidino)propoxy]phenyl]-1-(methylsulfonyl)-1H-indole

The title compound was obtained (180 mg) by the same general method as Example 1 by substituting 1-(3-hydroxypropyl)-2-pyrrolidineone for 3-(piperdin-1-yl) propanol in Step F. MS (ESI) m/z 435 (M+Na); $^1$H-NMR (CDCl$_3$) δ 8.12 (d, 1H), 7.59 (d, 1H), 7.49 (d, 2H), 7.36 (m, 2H), 6.95 (d, 2H), 6.67 (s, 1H), 4.03 (t, 2H), 3.55–3.35 (m, 6H), 2.72 (s, 3H), 2.40 (m, 2H), 2.06 (m, 2H).

Example 13

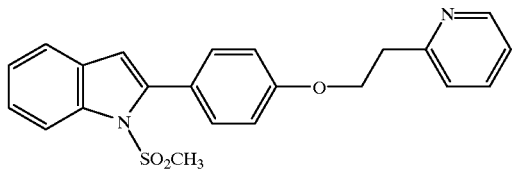

2-[4-[2-(2-Pyridinyl)ethoxyphenyl]-1-(methylsulfonyl)-1H-indole

The title compound was obtained (90 mg) by the same general method as Example 1 by substituting 2-(2-hydroxyethyl)pyridine for 3-(piperdin-1-yl)propanol in Step F. MS (ESI) m/z 393 (MH$^+$); $^1$H-NMR (CDCl$_3$) δ 8.59 (d, 1H), 8.12 (d, 1H), 7.67 (d, 1H), 7.59 (d, 1H), 7.48 (d, 2H), 7.35 (m, 2H), 7.20 (m, 2H), 6.97 (d, 2H), 6.66 (s, 1H), 4.43 (t, 2H), 3.32 (t, 2H), 2.72 (s, 3H).

Example 14

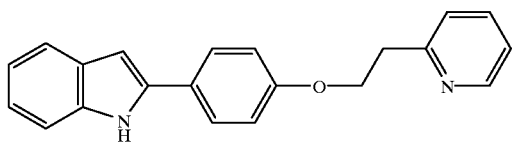

2-[4–12-(2-Pyridinyl)ethoxyphenyl]-1H-indole

The title compound was obtained (14.5 mg) by the same general method as Example 11 by substituting the product of Example 13 for the product of Example 10 as the starting material. MS (ESI) m/z 315 (MH$^+$); $^1$H-NMR (CDCl$_3$) δ 8.52 (d, 1H), 8.45 (bs, 1H), 7.58 (t, 1H), 7.53 (d, 1H), 7.50 (d, 2H), 7.29 (d, 1H), 7.22 (d, 1H), 7.12 (t, 1H), 7.08 (t, 1H), 7.01 (t, 1H), 6.88 (d, 2H), 6.63 (s, 1H), 4.32 (t, 2H), 3.21 (t, 2H).

Example 15

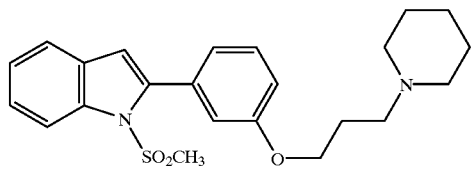

2-[3-[3-Piperidinopropoxy]phenyl)-1-(methylsulfonyl)-1H-indole $K_i$=33 nM

The title compound was obtained (84 mg) by the same general method as Example 1 by substituting 3-hydroxybenzaldehyde for 4-hydroxybenzaldehyde in Step B. MS (ESI) m/z 413 (MH$^+$); $^1$H-NMR (CDCl$_3$) δ 8.14 (d, 1H), 7.62 (d, 1H), 7.37 (m, 3H), 7.16 (d, 1H), 7.12 (s, 1H), 6.98 (d, 1H), 6.74 (s, 1H), 4.08 (t, 2H), 2.77 (s, 3H), 2.62 (t, 2H), 2.55 (m, 2H), 2.10 (m, 2H), 1.69 (m, 4H), 1.50 (m, 1H).

Example 16

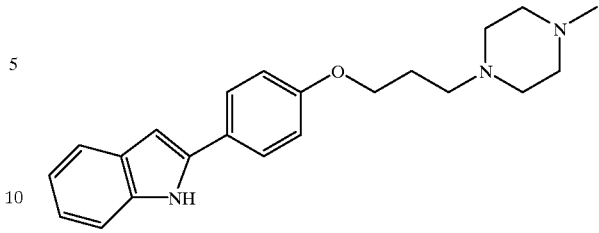

2-(4-(3-(4-Methylpiperazino)propoxy)phenyl)indole $K_i$=2000 nM

Step A Preparation of 4'-(3-chloropropoxy)acetophenone

A solution of 4'-hydroxyacetophenone (20 mmol, 2.72 g), 3-bromopropionyl chloride (21 mmol, 2.07 mL) and potassium carbonate (4.14 g, 30.0 mmol) in acetone (50 mL) was heated at reflux for overnight. The salt was filtered off. The solvent was evaporated. After drying in vacuo, the title compound (4.24 g) was collected.

Step B Preparation of 2-(4-(3-chloropropoxy)phenyl)indole

A mixture 4'-(3-chloropropoxy)acetophenone (10 mmol, 2.12 g) and phenylhydazine (10 mmol, 1.08 g)was heated at 100° C. for 40 min. Then PPA (~5 g) was added and temperature was raised to 130° C. and kept for 10 min. The mixture was cooled down. Water (50 mL) was added. After 2 h, greenish solid was formed and collected via filtration. The solid then was washed by a small amount of methanol (5 mL). After drying in vacuo, the title compound (1.5 g) was obtained.

Step C 2-(4-(3-(4-Methylpiperazino)propoxy)phenyl)indole

The mixture of (2-(4-(3-chloropropoxy)phenyl)indole (1 mmol, 285 mg) and 4-methylpiperazine (2 mL) was heated at 80° C. for 5 h. After concentration, the residue was purified by column chromatography (MeOH/CH$_2$Cl$_2$) afforded the title compound (285 mg): $^1$H NMR (CDCl$_3$, 400 MHz) δ 8.26 (s, 1H), 7.53 (m, 3H), 7.32 (bd, 1H, J=8.1 Hz), 7.1 (td, 1H, J=1.1, 7.0 Hz), 7.05 (td, 1H, J=1.1, 7.0 Hz), 6.90 (m, 2H), 6.64 (m, 1H), 3.99 (t, 2H, J=6.3 Hz), 2.48 (m, 10H, J=6.4 Hz), 2.25 (s, 3H), 1.93 (quintet, 2H, J=6.3 Hz); EIMS m/z 350 (M+H$^+$).

Example 17

1-(Methylsulfonyl)-2-(4-(3-(4-methylpiperazino)propoxy)phenyl)indole $K_i$=3000 nM Step A Preparation of 4-(3-chloropropoxy)benzaldehyde A solution of 4-hydroxybenzaldehyde (100 mmol, 12.2 g), 3-bromopropionyl chloride (101 mmol, 20 mL) and potassium carbonate (20.7 g, 150 mmol) in acetone (250 mL) was heated at reflux for overnight. The salt was filtered off. The solvent was evaporated. Reduced pressure distillation provided the title compound (15 g).

Step B Preparation of 1-ethynyl-4-(3-chloropropoxy) benzene

To LDA (2M in THF, 15 mL) in THF (100 mL) at −78° C., TMSCHN$_2$ (2M in hexanes, 15 mL) was added dropwisely. Ten minutes later, 4-(3-chloropropoxy)benzaldehyde (0.025 mol, 4.97 g) in THF (60 mL) was added. After 1 h stirring at −78° C., the mixture was warmed up and refluxed for 3 h. Water (250 mL) was added and extracted by EtOAc (2×200 mL). After being dried over Na$_2$SO$_4$ and concentration, the title compound (4.8 g) was obtained.

Step C Preparation of 1-ethylnyl-4-(3-(4-methylpiperazino) propoxy)benzene

The mixture of 1-ethynyl-4-(3-chloropropoxy)benzene (2 mmol, 388 mg) and 4-methylpiperazine (2 mL) was heated at 80° C. for 5 h. After concentration, the residue was purified by column chromatography (MeOH/CH$_2$Cl$_2$) afforded the title compound (400 mg).

Step D Preparation of 2-iodo-N-(methanesulfonyl)aniline

To the mixture of the 2-iodo-4-chloroaniline (5.0 g, 20 mmol) and triethylamine (8.3 mL, 60 mmol) in methylene chloride (200 mL), the solution of methanesulfonyl chloride (3.4 mL, 44 mmol) was added slowly. The solution then was stirred at room temperature for 2 h. After being washed by HCl solution (0.5 N, 2×100 mL), NaOH solution (0.5 N, 2×100 mL), brine (100 mL), the organic layer was dried over Na$_2$SO$_4$ and concentrated providing the title compound (6.6 g).

Step E Preparation of 1-(methylsulfonyl)-2-(4-(3-(4-methylpiperazino)propoxy)phenyl)indole The mixture of 1-ethynyl-4-(3-(4-methylpiperazino) propoxy)benzene (230 mg, 0.89 mmol), 2-iodo-N-(methanesulfonyl)aniline (0.89 mmol, 296 mg), CuI (17 mg, 0.089 mmol), Pd(PPh$_3$)$_2$Cl$_2$ (32 mg, 0.045 mmol) and triethylamine (0.5 mL) in DMF (5 mL) was stirred at 80° C. for overnight. After concentration, water (20 mL) was added and extracted by methlene chloride (3×20 mL). The organics was concentrated and purified by column chromatography afforded the title compound (260 mg): $^1$H NMR (CDCl$_3$, 400 MHz) δ 8.05 (d, 1H, J=8.8 Hz), 7.55 (d, 1H, J=2.1 Hz), 7.50 (td, 2H, J=8.8,2.1 Hz), 7.32 (d, 1H, J=2.1 Hz), 7.30 (d, 1H, J=2.1 Hz), 6.96 (td, 2H J=2.1, 8.8 Hz), 6.60 (d, 1H, J=0.5 Hz), 4.08 (t, 2H, J=6.3 Hz), 2.74 (s, H), 2.55 (m, 10H), 2.33 (s, 3H), 2.02 (quintet, 2H, J=6.3 Hz); EIMS m/z 462 (M+H$^+$).

F. BIOLOGICAL EXAMPLES

Biological Example 1

1(A) Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO$_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One μg supercoiled H$_3$ receptor cDNA was added to the cells and mixed. The voltage for the electroporation was set at 0.25 kV, the capacitance is set at 960 μF.

After electroporation the cells were diluted into 10 mL complete media and plated onto four 10 cm dishes. Due to the variability in the efficiency of electroporation, four different concentrations of cells were plated. The ratios used were: 1:20, 1:10, and 1:5, with the remainder of the cells being added to the fourth dish. The cells were allowed to recover for 24 hours before adding the selection media (complete media with 600 μg/ml G418). After 10 days dishes were analyzed for surviving colonies of cells. Dishes with well-isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

1(B) [3H]-N-methylhistamine Binding

Cell pellets from histamine H$_3$ receptor-expressing SK-N-MC cells were homogenized in 20 mM TrisHCl/0.5 mM EDTA. Supernatants from a 800 g spin were collected, reccentrifuged at 30,000 g for 30 minutes. Pellets were rehomogenized in 50 mM Tris/5 mM EDTA (pH 7.4). Membranes were incubated with 0.8 nM [$^3$H]-N-methylhistamine plus/minus test compounds for 45 minutes at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 μM histamine. PK$_i$ values were calculated based on a K$_D$ of 800 μM and a ligand concentration ([L]) of 800 μM according to the formula:

$$K_i = (IC_{50})/(1+([L]/(K_D)))$$

G. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A compound of the following formula:

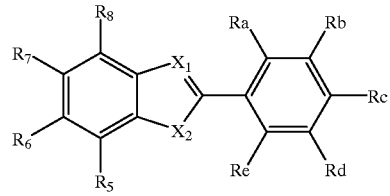

wherein X$_1$ is CH; and X$_2$ is NR$_3$; R$_3$ is H, or —SO$_2$ (C$_{1-6}$ alkyl);

and one of Ra, Rb, Rc, Rd, and Re is WZ; and the others are of Ra, Rb, Rc, Rd, and Re being H;

and W is —O—, or O—R$_9$ wherein R$_9$ is C$_{1-6}$ alkylene;

and Z is NR$_{11}$R$_{12}$ wherein each of R$_{11}$ and R$_{12}$ is independently from H, C$_{1-6}$ alkyl;

or Z is piperidinyl, pyrrolidinyl, or pyridinyl, optionally substituted with one methyl or oxo moiety.

2. A compound of claim 1, wherein R$_3$ is H or —SO$_2$ (C$_{1-3}$ alkyl).

3. A compound of claim 1, wherein R$_3$ is —SO$_2$(C$_{1-3}$ alkyl).

4. A compound of claim 1, wherein R$_3$ is methylsulfonyl.

5. A compound of claim 1, wherein W is ethoxy, propoxy, or butoxy.

6. A compound of claim 1, wherein W is —O—.

7. A compound of claim 1, wherein $R_e$ is WZ; W is propoxy or ethoxy; and Z is N-piperidino, or 2-(N-methyl)pyrrolidino.

8. A compound of claim 7, selected from 2-[4-[2-[1-(methyl)-2-pyrrolidinyl]ethoxy]phenyl)-1H-indole, 2-[4-[2-[1-(methyl)-2-pyrrolidinyl]ethoxy]phenyl)-1-(methylsulfonyl)-1H-indole; or a pharmaceutically acceptable salt, amide, ester, or hydrate thereof.

9. A compound of claim 1 selected from 2-[4-[1-(methyl)-4-piperidinyl]oxyphenyl]-1-(methylsulfonyl)-1H-indole; 2-[4-[1-(methyl)-4-piperidinyl]oxyphenyl]-1H-indole; 2-[4-[4-pyridinyl]methoxyphenyl]-1-(methylsulfonyl)-1H-indole; 2-[4-[2-(2-pyridinyl)ethoxyphenyl]-1-(methylsulfonyl)-1H-indole; and 2-[4-[2-(2-pyridinyl)ethoxyphenyl]-1H-indole; or a pharmaceutically acceptable salt, amide, ester, or hydrate thereof.

10. A pharmaceutical composition comprising a compound of claim 1 and a pharmaceutically acceptable carrier.

11. A pharmaceutical composition of claim 10, wherein said compound has a formula selected from 2-[4-[1-(methyl)-4-piperidinyl]oxyphenyl]-1-(methylsulfonyl)-1H-indole; 2-[4-[1-(methyl)-4-piperidinyl]oxyphenyl]-1H-indole; 2-[4-[4-pyridinyl]methoxyphenyl]-1-(methylsulfonyl)-1H-indole; 2-[4-[2-(2-pyridinyl)ethoxyphenyl]-1-(methylsulfonyl)-1H-indole; and 2-[4-[2-(2-pyridinyl)ethoxyphenyl]-1H-indole; or a pharmaceutically acceptable salt, amide, ester, or hydrate thereof.

12. A pharmaceutical composition of claim 10, wherein said compound has a formula selected from 2-[4-[2-[1-(methyl)-2-piperidinyl]ethoxy]phenyl-1-indole; 2-[4-[2-[1-(methyl)-2-piperidinyl]ethoxy]phenyl)-1-(methylsulfonyl)-1-H-indole; and 2-[3-[3-piperidinopropoxy]phenyl]-1(methylsulfonyl)-1H-indole; or a pharmaceutically acceptable salt, amide, ester, or hydrate thereof.

* * * * *